(12) United States Patent
Shimizu et al.

(10) Patent No.: US 6,818,262 B2
(45) Date of Patent: Nov. 16, 2004

(54) FILTERS FOR ELECTRONIC DISPLAY DEVICE

(75) Inventors: Ikuo Shimizu, Yokkaichi (JP); Motoharu Kinugasa, Yokkaichi (JP); Hiroshi Toyoda, Yokkaichi (JP); Shiho Yamada, Yokkaichi (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 15 days.

(21) Appl. No.: 10/347,887

(22) Filed: Jan. 22, 2003

(65) Prior Publication Data

US 2003/0165640 A1 Sep. 4, 2003

(30) Foreign Application Priority Data

Jan. 30, 2002 (JP) ........................................ 2002-021106
Jul. 4, 2002 (JP) ........................................ 2002-195457

(51) Int. Cl.[7] ........................... G02B 5/22; C07D 403/08
(52) U.S. Cl. ..................................... 428/1.31; 548/364.1
(58) Field of Search ...................... 428/1.31; 548/364.1, 548/306.1

(56) References Cited

U.S. PATENT DOCUMENTS 6,558,768 B2 * 5/2003 Noguchi et al. ............ 428/64.1
6,596,364 B2 * 7/2003 Shimizu et al. ............. 428/64.1
6,638,624 B2 * 10/2003 Ozawa .................... 428/411.1

FOREIGN PATENT DOCUMENTS

| EP | 1 152 001 | 11/2001 |
| EP | 1 157 990 | 11/2001 |
| EP | 1 160 230 | 12/2001 |
| JP | 2000-345059 | 12/2000 |
| JP | 2001-192350 | 7/2001 |

* cited by examiner

Primary Examiner—Fiona T. Powers
(74) Attorney, Agent, or Firm—Fitzpatrick, Cella, Harper & Scinto

(57) ABSTRACT

The present invention provides filters for an electronic display device comprising a squarylium compound represented by the general formula (I):

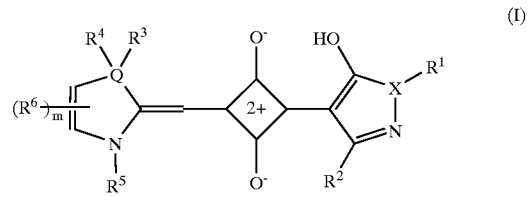

wherein X represents a nitrogen atom or an oxygen atom; Q represents a carbon atom, a nitrogen atom, an oxygen atom or a sulfur atom; and $R^1$, $R^2$, $R^3$, $R^4$, $R^5$, $R^6$ and m are as defined in the specification. The filters for an electronic display device of the present invention can selectively shield the light having such a wavelength that reduces the color purity, and thereby can provide clear images.

3 Claims, No Drawings

FILTERS FOR ELECTRONIC DISPLAY DEVICE

FIELD OF THE INVENTION

The present invention relates to a filter for an electronic display device which can selectively shield the light having such a wavelength that reduces the color purity.

BACKGROUND OF THE INVENTION

An electronic display device displays color images by a combination of three primary colors: red, blue, and green. However, in actual devices, there was a problem that images with low color purity are made because of containing additional lights other than the three primary colors (e.g. for plasma display panels, the additional lights are those of 550–600 nm: neon emission). To solve this problem, it has been devised to equip the devices with a filter having a color compensating function. It is known to use a squarylium compound as a pigment for a filer for an electronic display device. For example, Japanese Published Unexamined Patent Application No. 192350/01 discloses a plasma display panel which contains a squarylium compound represented by the following formula, or the like.

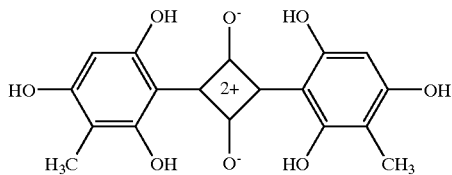

However, the above plasma display panel is not practically satisfactory in that a transmittance of the light is insufficient at a wavelength region around 500 nm.

OBJECTS OF THE INVENTION

An object of the present invention is to provide a filter for an electronic display device which can selectively shield the light having such a wavelength that reduces the color purity, and thereby can provide clear images.

SUMMARY OF THE INVENTION

The present invention provides the following [1]–[7]:

[1] A filter for an electronic display device comprising a squarylium compound represented by the general formula (I):

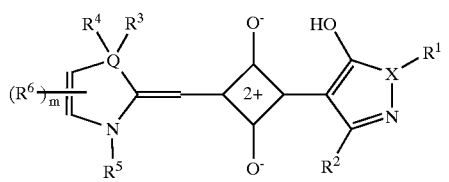

wherein X represents a nitrogen atom or an oxygen atom; Q represents a carbon atom, a nitrogen atom, an oxygen atom or a sulfur atom; $R^1$ represents a hydrogen atom, an alkyl group optionally having substituent(s), an aryl group optionally having substituent(s), an aralkyl group optionally having substituent(s), or a heterocycle group optionally having substituent(s), provided that when X is an oxygen atom, then $R^1$ is absent; $R^2$ represents a hydrogen atom, a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s); $R^3$ and $R^4$ are the same or different, and represent a hydrogen atom, an alkyl group optionally having substituent(s), an aryl group optionally having substituent (s), an aralkyl group optionally having substituent(s), or a heterocycle group optionally having substituent(s), or $R^3$ and $R^4$ may be taken together with an adjacent carbon atom to form an alicyclic hydrocarbon ring optionally having substituent(s), or an heterocyclic ring optionally having substituent(s), provided that when Q is a nitrogen atom, then $R^4$ is absent and, when Q is an oxygen atom or a sulfur atom, then $R^3$ and $R^4$ are absent; $R^5$ represents a hydrogen atom, an alkyl group optionally having substituent(s), an aryl group optionally having substituent(s), an aralkyl group optionally having substituent(s), or a heterocycle group optionally having substituent(s); $R^6$ represents a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s); and m represents an integer of 0–2, wherein when m is 2, then respective $R^6$s may be the same or different, or further two $R^6$s may be taken together with two carbon atoms to which each $R^6$ is adjacent to form an aromatic ring optionally having substituent(s).

[2] A filter for an electronic display device comprising a squarylium compound represented by the general formula (Ia):

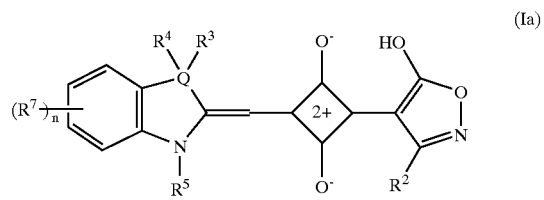

wherein $R^2$, $R^3$, $R^4$ and $R^5$ are as defined above, respectively; $R^7$ represents a halogen atom, an alkyl group optionally having substituent(s), an alkoxyl group optionally having substituent(s), an aralkyl group optionally having substituent(s), an aryl group optionally having substituent (s), a nitro group, a cyano group, a hydroxyl group, an amino group optionally having substituent(s), or a heterocycle group optionally having substituent(s); and n represents an integer of 0–4, wherein when n is 2–4, then respective $R^7$s may be the same or different, or further adjacent two $R^7$s may be taken together with two carbon atoms to which each $R^7$ is adjacent to form an aromatic ring optionally having substituent(s).

[3] A filter for an electronic display device comprising a squarylium compound represented by the general formula (Ib):

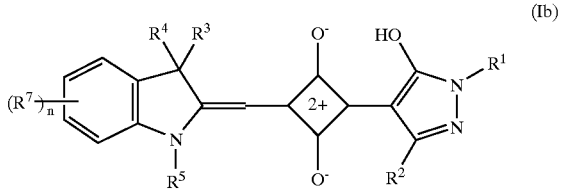

(Ib)

wherein $R^1$, $R^2$, $R^3$, $R^4$, $R^5$, $R^7$ and n are as defined above, respectively.

[4] A filter for an electronic display device comprising a squarylium compound represented by the general formula (Ic):

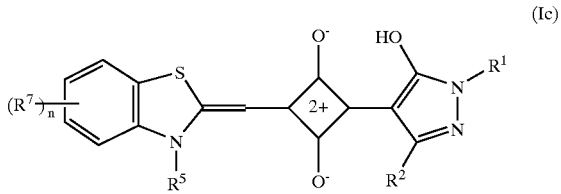

(Ic)

wherein $R^1$, $R^2$, $R^5$, $R^7$ and n are as defined above, respectively.

[5] A filter for an electronic display device comprising a squarylium compound represented by the general formula (Id):

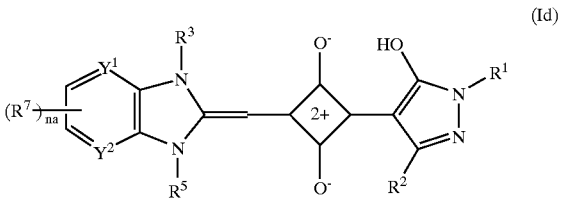

(Id)

wherein $R^1$, $R^2$, $R^3$, $R^5$ and $R^7$ are as defined above, respectively; $Y^1$ and $Y^2$ are the same or different, and represent a carbon atom or a nitrogen atom; and na represents an integer of 0–4, provided that when one of $Y^1$ and $Y^2$ is a nitrogen atom and the other is a carbon atom; then na represents an integer of 0–3, and when both of $Y^1$ and $Y^2$ are nitrogen atoms, then na represents an integer of 0–2.

[6] The filter for an electronic display device according to any one of [1]–[5], which further comprises a binder.

[7] A squarylium compound represented by the general formula (Ia):

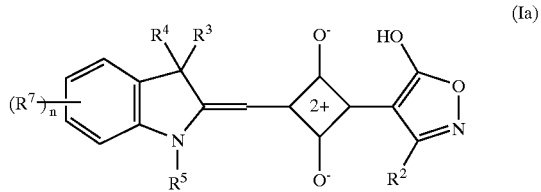

(Ia)

wherein $R^2$, $R^3$, $R^4$, $R^5$, $R^7$ and n are as defined above, respectively.

DETAILED DESCRIPTION OF THE INVENTION

Hereinafter, the compound represented by the general formula (I) is referred to as compound (I). Compounds with other formula numbers are also expressed in the same manner.

In the definition of each group in the general formula (I) and general formulas (Ia)–(Id), examples of the alkyl group and an alkyl moiety in the alkoxyl group include linear or branched alkyl groups having 1–6 carbon atom(s) and cyclic alkyl groups having 3–8 carbon atoms, specifically, such as a methyl group, an ethyl group, a propyl group, an isopropyl group, a butyl group, an isobutyl group, a sec-butyl group, a tert-butyl group, a pentyl group, an isopentyl group, a 2-methylbutyl group, a tert-pentyl group, a hexyl group, a cyclopropyl group, a cyclobutyl group, a cyclopentyl group, a cyclohexyl group, a cycloheptyl group and a cyclooctyl group.

Examples of the aralkyl group include aralkyl groups having 7–15 carbon atoms, specifically, such as a benzyl group, a phenethyl group, a phenylpropyl group and a naphthylmethyl group.

Examples of the aryl group include a phenyl group, a naphthyl group, an anthryl group, and the like.

Examples of the halogen atom include a fluorine atom, a chlorine atom, a bromine atom and an iodine atom.

Examples of the aromatic ring formed by two $R^6$s taken together with two carbon atoms to which each $R^6$ is adjacent, and the aromatic ring formed by adjacent two $R^7$s taken together with two carbon atoms to which each $R^7$ is adjacent, include an aromatic heterocyclic ring described below and the like, in addition to a benzene ring, a naphthalene ring and the like.

Examples of the heterocyclic ring in the heterocycle group and the heterocyclic ring formed by $R^3$ and $R^4$ taken together with an adjacent carbon atom, include an aromatic heterocyclic ring and an alicyclic heterocyclic ring.

Examples of the aromatic heterocyclic ring include 5- or 6-membered monocyclic aromatic heterocyclic rings containing at least one atom selected from a nitrogen atom, an oxygen atom and a sulfur atom, and fused bicyclic or tricyclic aromatic heterocyclic rings containing at least one atom selected from a nitrogen atom, an oxygen atom and a sulfur atom wherein 3- to 8-membered rings are fused, more specifically, such as a pyridine ring, a pyrazine ring, a pyrimidine ring, a pyridazine ring, a quinoline ring, an isoquinoline ring, a phthalazine ring, a quinazoline ring, a quinoxaline ring, a naphthylidine ring, a cinnoline ring, a pyrrole ring, a pyrazole ring, an imidazole ring, a triazole ring, a tetrazole ring, a thiophene ring, a furan ring, a thiazole ring, an oxazole ring, an indole ring, an isoindole ring, an indazole ring, a benzimidazole ring, a benzotriazole ring, a benzothiazole ring, a benzoxazole ring, a purine ring and a carbazole ring.

Examples of the alicyclic heterocyclic ring include 5- or 6-membered aromatic monocyclic heterocyclic rings containing at least one atom selected from a nitrogen atom, an oxygen atom and a sulfur atom, and fused bicyclic or tricyclic aromatic heterocyclic rings containing at least one atom selected from a nitrogen atom, an oxygen atom and a sulfur atom wherein 3- to 8-membered rings are fused, more specifically, such as a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, a tetrahydroisoquinoline ring, a tetrahydrofuran ring, a tetrahydropyran ring, a dihydrobenzofuran ring and a tetrahydrocarbazole ring.

Examples of the alicyclic hydrocarbon ring formed by $R^3$ and $R^4$ taken together with an adjacent carbon atom, include alicyclic hydrocarbon rings having 3–8 carbon atoms which may be saturated or unsaturated, specifically, such as a cyclopropane ring, a cyclobutane ring, a cyclopentane ring, a cyclohexane ring, a cycloheptane ring, a cyclooctane ring, a cyclopentene ring, a 1,3-cyclopentadiene ring, a cyclohexane ring and a cyclohexadiene ring.

Examples of substituents of the aralkyl group, the aryl group, the alkoxyl group, the alicyclic hydrocarbon ring formed by $R^3$ and $R^4$ taken together with an adjacent carbon atom, the heterocyclic ring formed by $R^3$ and $R^4$ taken together with an adjacent carbon atom, and the aromatic ring and the heterocycle group formed by adjacent two $R^7$s taken together with two carbon atoms to which each $R^7$ is adjacent, include 1–5 substituents which are the same or different, specifically, such as a hydroxyl group, a carboxyl group, a halogen atom, an alkyl group, an alkoxyl group, a nitro group and a trifluoromethyl group. The halogen atom, the alkyl group and the alkoxyl group are as defined above, respectively.

Examples of substituents of the alkyl group include 1–3 substituents which are the same or different, specifically, such as a hydroxyl group, a carboxyl group, a halogen atom and an alkoxyl group. The halogen atom and the alkoxyl group are as defined above, respectively.

Examples of substituents of the amino group include 1–2 alkyl groups which are the same or different, and the alkyl group in this case is as defined above.

Examples of substituents of the aromatic ring formed by two $R^6$s taken together with two carbon atoms to which each $R^6$ is adjacent, include a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), a heterocycle group optionally having substituent(s), and the like, and the halogen atom, the alkyl group optionally having substituent(s), the alkoxyl group optionally having substituent(s), the aralkyl group optionally having substituent(s), the aryl group optionally having substituent(s), the amino group optionally having substituent(s), and the heterocycle group optionally having substituent(s) are as defined above, respectively.

A compound (I) can be prepared by or in a method similar to the known method (WO 01/44233 etc.), and a compound (Ia) may also be prepared by the following method for preparation.

Method for preparation of a compound (Ia)

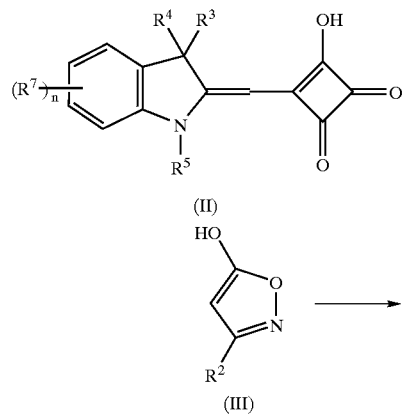

(II)

(III)

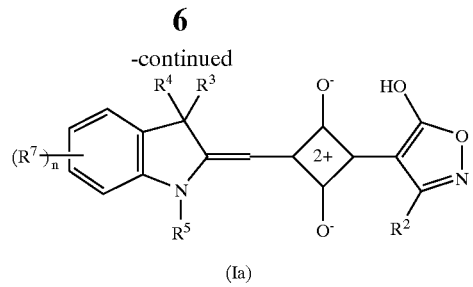

(Ia)

wherein $R^2$, $R^3$, $R^4$, $R^5$, $R^7$ and n are as defined above, respectively.

A compound (II) can be prepared by or in a method similar to the known method [Dyes and Pigments, 21, 227 (1993) etc.] A compound (III) can be prepared by or in a method similar to the known method (Japanese Published Unexamined Patent Application No. 242526/89).

The compound (Ia) can be obtained by reacting the compound (II) with 0.5 to 2-fold mole of the compound (III) at 80–120° C. for 1–15 hours in a solvent. The solvent is not particularly limited, but an alcohol such as ethanol, propanol, isopropyl alcohol, butanol or octanol, or a mixed solvent (containing a not less than 50% volume/volume alcohol) of the above alcohol and an aromatic hydrocarbon such as benzene, toluene or xylene is preferable.

After the reaction, if necessary, the desired compound may be purified by a procedure normally used in synthetic organic chemistry (column chromatography, recrystallization, washing with a solvent, etc.)

Preferable embodiments of the compound (I) are illustrated below in Tables 1-1 and 1-2, and the following formulas (compounds 43–46). In Tables and the structural formulas of compounds 43–46, Me represents a methyl group, Pr represents a propyl group, iPr represents an isopropyl group, Bu represents a butyl group, tBu represents a tert-butyl group, Ph represents a phenyl group and Z represents —CH═CH—CH═CH—.

TABLE 1-1

Examples of compound (Ib)

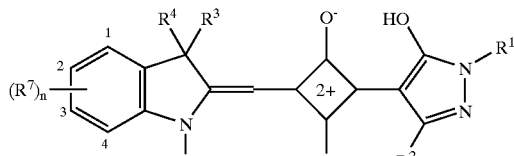

| Compound | $R^1$ | $R^2$ | $R^3$ | $R^4$ | $R^5$ | n | $R^7$ |
|---|---|---|---|---|---|---|---|
| 1 | Ph | Pr | Me | Me | Me | 1 | 2-Cl |
| 2 | Ph | iPr | Me | Me | Me | 1 | 2-Cl |
| 3 | Me | Pr | Me | Me | Me | 1 | 2-Cl |
| 4 | Ph | Me | Me | Me | Me | 0 | — |
| 5 | Ph | Me | Me | Me | Me | 1 | 2-Cl |
| 6 | Me | iPr | Me | Me | Me | 1 | 2-Cl |
| 7 | Ph | Pr | Me | Me | Me | 1 | 2-Br |
| 8 | 3-MeC$_6$H$_4$ | Me | Me | Me | Me | 1 | 2-Cl |
| 9 | 4-MeC$_6$H$_4$ | Me | Me | Me | Me | 1 | 2-Cl |
| 10 | 3-MeC$_6$H$_4$ | Pr | Me | Me | Me | 0 | — |
| 11 | 3-MeC$_6$H$_4$ | Pr | Me | Me | Me | 1 | 2-Cl |
| 12 | 4-MeC$_6$H$_4$ | Pr | Me | Me | Me | 1 | 2-Cl |
| 13 | Ph | Pr | Me | Me | Me | 2 | 1-Z-2 |
| 14 | 4-BrC$_6$H$_4$ | Pr | Me | Me | Me | 1 | 2-Cl |
| 15 | 4-BrC$_6$H$_4$ | Pr | Me | Me | Me | 2 | 1-Z-2 |
| 16 | 4-ClC$_6$H$_4$ | Pr | Me | Me | Me | 2 | 1-Z-2 |
| 17 | Ph | Ph | Me | Me | Me | 1 | 2-Cl |
| 18 | 4-MeOPh | Ph | Me | Me | Me | 1 | 2-Cl |

TABLE 1-1-continued

Examples of compound (Ib)

| Compound | R¹ | R² | R³ | R⁴ | R⁵ | n | R⁷ |
|---|---|---|---|---|---|---|---|
| 19 | 4-ClC₆H₄ | Pr | Me | Me | Me | 1 | 2-Cl |
| 20 | 3-ClC₆H₄ | Pr | Me | Me | Me | 1 | 2-Cl |

TABLE 1-2

Examples of compound (Ib)

| Compound | R¹ | R² | R³ | R⁴ | R⁵ | n | R⁷ |
|---|---|---|---|---|---|---|---|
| 21 | Ph | CF₃ | Me | Me | Me | 2 | 1-Z-2 |
| 22 | 3-ClC₆H₄ | Pr | Me | Me | Me | 2 | 1-Z-2 |
| 23 | 4-FC₆H₄ | Pr | Me | Me | Me | 2 | 1-Z-2 |
| 24 | 4-FC₆H₄ | Me | Me | Me | Me | 1 | 2-Cl |
| 25 | 4-CF₃C₆H₄ | Pr | Me | Me | Me | 1 | 2-Cl |
| 26 | 4-ClC₆H₄ | Me | Me | Me | Me | 2 | 1-Z-2 |
| 27 | 4-FC₆H₄ | Me | Me | Me | Me | 2 | 1-Z-2 |
| 28 | 4-CF₃C₆H₄ | Pr | Me | Me | Me | 2 | 1-Z-2 |
| 29 | Ph | Pr | Me | Me | Me | 1 | 2-MeO |
| 30 | Ph | CF₃ | Me | Me | Me | 1 | 2-Cl |
| 31 | Me | Me | Me | Me | Me | 2 | 1-Z-2 |
| 32 | Ph | Pr | Me | Me | H | 0 | — |
| 33 | Ph | CF₃ | Me | Me | Me | 1 | 2-MeO |
| 34 | Ph | CF₃ | Me | Me | Me | 1 | 2-Me |
| 35 | Ph | CF₃ | (CH₂)₅ | | Me | 0 | — |
| 36 | Ph | Pr | Me | Me | Me | 2 | 2,4-Cl₂ |
| 37 | Ph | Pr | (CH₂)₅ | | Me | 1 | 2-Cl |
| 38 | Ph | CF₃ | Me | Me | Bu | 1 | 2-Cl |
| 39 | tBu | Pr | Me | Me | Bu | 1 | 2-Cl |
| 40 | Ph | iPr | Me | Et | Me | 1 | 2-Cl |
| 41 | tBu | Me | Me | Me | Me | 2 | 1-Z-2 |
| 42 | tBu | Ph | Me | Me | Me | 2 | 2-Cl |

Compound 43

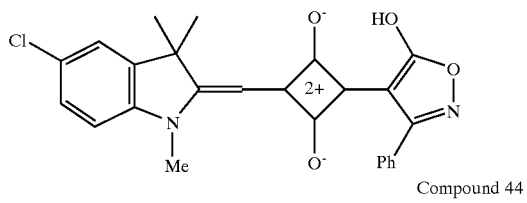

Compound 44

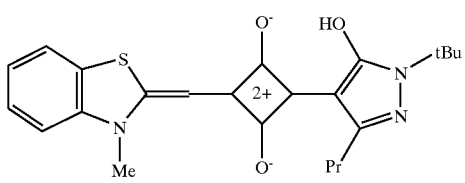

Compound 45

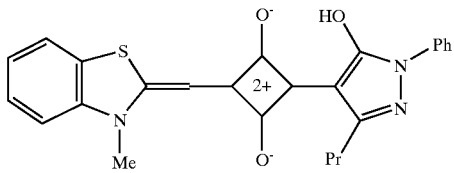

Compound 46

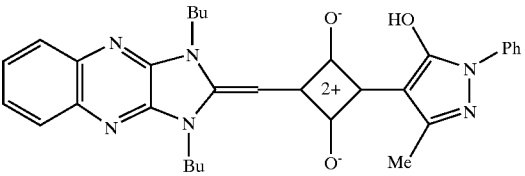

Then, the filter for an electronic display device of the present invention will be explained.

It is preferable that the compound (I) used for the filter for an electronic display device of the present invention has an absorption maximum in an absorption region of 550–610 nm, more preferably 570–600 nm in a chloroform solution. It is also preferable that the film containing the compound (I) has an absorption maximum in an absorption region of 550–610 nm, more preferably 570–610 nm. The film containing the compound (I) is prepared by directly dissolving or dispersing the compound (I) is a resin constituting a clear substrate, followed by forming the mixture into the film. It is also preferable that an absorption width of 50% transmittance at an absorption maximal wavelength (a difference between maximal and minimal absorption wavelengths which show not more than 50% of transmittance near the absorption maximal wavelength; the absorption maximal wavelength means wavelength showing maximal absorption) is not more than 80 nm. It is also preferable that the compound (I) has a sufficient transmittance in a region of 400–500 nm, and, for example, in the case of the compound (I) having an absorption maximum in a region of 550–610 nm, it is preferable that the transmittance at 500 nm is not less than 80%.

The filter for an electronic display device of the present invention preferably has logarithm of a molar extinction coefficient of not less than 4.5, more preferably not less than 4.8.

It is preferable that the filter for an electronic display device is prepared by applying a coating solution of the compound (I) to a clear substrate, and evaporating an organic solvent.

The coating solution may be prepared by dissolving a solution of an organic solvent containing the compound (I) with a binder in an organic solvent.

Examples of the organic solvent include ethers such as dimethoxyethane, methoxyethoxyethane, tetrahydrofuran and dioxane, ketones such as acetone, methyl ethyl ketone, methyl isobutyl ketone and cyclohexanone, and aromatic hydrocarbons such as benzene, toluene, xylene and monochlorobenzene, and it is preferable that the organic solvent is used in a 10 to 3000-fold amount (by weight) based upon the compound (I).

Examples of the binder include a polyester resin, a polycarbonate resin, a polyacrylic acid resin, a polystyrene resin, a polyvinyl chloride resin, a polyvinyl acetate resin and the like, and it is preferable that the binder is used in a 10 to 500-fold amount (by weight) based upon the compound (I).

The clear substrate is not particularly limited as far as it is a clear resin or glass having low absorption and scattering, and examples of the resin include a polyester resin, a polycarbonate resin, a polyacrylic acid resin, a polystyrene resin, a polyvinyl chloride resin, a polyvinyl acetate resin and the like.

As a procedure for applying a coating solution of the compound (I) to the clear substrate, the known applying method such as a bar coating method, a spraying method, a roll coating method or a dipping method can be utilized (U.S. Pat. No. 2,681,294 etc.)

The compound (I) has the high solubility in an organic solvent and is suitable for a method of preparing a filter of an electronic display device using the above-mentioned coating solution.

The filter for an electronic display device of the present invention may also be prepared by directly dissolving or dispersing the compound (I) in a resin constituting a clear substrate, followed by forming the mixture into a film, and, if necessary, laminating the film with other clear substrates.

Since the filter for an electronic display device of the present invention can selectively shield the light having such a wavelength that reduces the color purity while maintaining the brightness of the image, it is excellent in the color correcting function. Therefore, the above filter can provide a clear image excellent in colors.

The filter for an electronic display device of the present invention can be employed for, for example, a cathode-ray tube, a fluorescent display tube, an electroluminescence panel, a light emitting diode, a plasma panel, an incandescent lamp, a laser display, a liquid crystal display, an electrochromic display or the like.

EXAMPLES

Example 1 n-Butanol (20 ml) and 10 ml of toluene were added to 1.22 g of 4-(5-chloro-1,3,3-trimethylindolin-2-ylidenemethyl)-3-hydroxy-3-cyclobutene-1,2-dione and 0.64 g of 5-hydroxy-3-phenylisooxazole, the mixture was heated at 110° C. for 10 hours, and the precipitate was collected by filtration, and purified by a chromatography method (silica gel, chloroform/methanol) to obtain Compound 43 (0.67 g).

$^1$H NMR δ (DMSO-$d_6$) ppm : 1.58 (6H, s), 3.50 (3H, s), 5.55 (1H, s), 7.31–7.50 (7H, m), 7.61–7.62 (1H, m).

Reference Example 1 n-Butanol (3 ml) and 1.5 ml of toluene were added to 0.54 g of 3-(1-tert-butyl-5-hydroxy-3-propylpyrazol-4-yl)-4-hydroxycyclobutene-1,2-dione, 0.60 g of 2,3-dimethylbenzothiazolium iodide and 0.28 g of quinoline, the mixture was heated at 110° C. for 5 hours, 5 ml of methanol was added thereto, and the precipitate was collected by filtration to obtain Compound 44 (0.64 g).

$^1$H NMR δ (CDCl$_3$) ppm : 0.99 (3H, t, J=7.3 Hz), 1.59 (9H, s), 1.65–1.75 (2H, m), 2.81–2.85 (2H, m), 3.80 (3H, s), 5.94–6.04 (1H, br s), 7.32–7.37 (2H, m), 7.46–7.50 (1H, m), 7.66–7.68 (1H, m)

Reference Example 2 n-Butanol (4 ml) and 2 ml of toluene were added to 0.52 g of 3-hydroxy-4-(5-hydroxy-3-methyl-1-phenylpyrazol-4-yl)cyclobutene-1,2-dione, 1.19 g of 1,3-dibutyl-2-methylimidazo[4,5-b]quinoxalium iodide and 0.35 g of quinoline, the mixture was heated at 110° C. for 8 hours, 10 ml of methanol was added thereto, and the precipitate was collected by filtration to obtain Compound 46 (0.77 g).

$^1$H NMR δ (CDCl$_3$) ppm : 0.96 (6H, t, J=7.6 Hz), 1.33–1.43 (4H, m), 1.82–1.90 (4H, m), 2.50 (3H, s), 3.56 (3H, s), 4.76 (4H, t, J=7.3 Hz), 5.74 (1H, s), 7.74–7.78 (2H, m), 8.09–8.14 (2H, m).

Example 2

An absorption maximum wavelength (λmax) and logarithm of a molar extinction coefficient (logε) of Compounds 1–29, 31, 32, and 36–46 in a chloroform solution were measured (800–300 nm), and the results are shown in Tables 2-1 and 2-2. Compounds 1–29, 31, 32 and 36–42 can be prepared in a manner similar to the method described in WO01/44233 or the like.

TABLE 2-1

Spectroscopic property of squarylium compounds

| Compound | Spectroscopic property (Chloroform solution) | |
|---|---|---|
| | λ max (nm) | log ε |
| 1 | 577.5 | 5.1 |
| 2 | 578.5 | 5.2 |
| 3 | 570.0 | 5.2 |
| 4 | 571.0 | 5.2 |
| 5 | 576.5 | 5.3 |
| 6 | 571.0 | 5.2 |
| 7 | 578.5 | 5.2 |
| 8 | 576.5 | 5.2 |
| 9 | 576.5 | 5.2 |
| 10 | 573.0 | 5.2 |
| 11 | 577.5 | 5.2 |
| 12 | 578.0 | 5.2 |
| 13 | 590.5 | 5.1 |
| 14 | 579.0 | 5.2 |
| 15 | 592.0 | 5.1 |
| 16 | 592.0 | 5.1 |
| 17 | 583.0 | 5.2 |

TABLE 2-2

Spectroscopic property of squarylium compounds

| Compound | Spectroscopic property (Chloroform solution) | |
|---|---|---|
| | λ max (nm) | log ε |
| 18 | 584.0 | 5.2 |
| 19 | 578.5 | 5.2 |
| 20 | 578.5 | 5.2 |
| 21 | 578.5 | 4.9 |
| 22 | 591.5 | 5.0 |
| 23 | 590.0 | 5.0 |
| 24 | 577.0 | 5.2 |
| 25 | 578.5 | 5.1 |
| 26 | 585.0 | 5.0 |
| 27 | 588.5 | 5.0 |
| 28 | 591.5 | 5.0 |
| 29 | 584.0 | 5.1 |
| 31 | 581.5 | 5.0 |
| 32 | 581.5 | 5.0 |
| 36 | 579.0 | 5.0 |
| 37 | 581.0 | 5.2 |
| 38 | 572.0 | 5.1 |
| 39 | 574.5 | 5.3 |
| 40 | 579.5 | 5.3 |
| 41 | 585.0 | 5.2 |
| 42 | 579.5 | 5.3 |
| 43 | 585.0 | 4.9 |
| 44 | 576.5 | 5.2 |

TABLE 2-2-continued

Spectroscopic property of squarylium compounds

| Compound | Spectroscopic property (Chloroform solution) | |
|---|---|---|
| | λ max (nm) | log ε |
| 45 | 577.0 | 5.2 |
| 46 | 595.0 | 5.2 |

Example 3

A 0.5% by weight solution of Compound 1, 13, 29, 41, 43, 44 or 46 in dimethoxyethane and a 20% by weight solution of a polyester resin [vylon 200 (manufactured by TOYOBO Co., Ltd.)] in dimethoxyethane were mixed at a ratio of 7:2 (6:2 in the case of Compound 41), and the mixture applied on a glass substrate by a barcoater, and dried to make a coated film. A transmittance curve of this film was measured (800–300 nm), followed by measuring an absorption maximum wavelength, an absorption width of 50% transmittance and a transmittance at 500 nm in the film. The results are shown in Table 3.

TABLE 3

Maximal absorption wavelengths, absorption widths of 50% transmittance, and transmittances at 500 nm of squarylium compounds in a film

| | Absorption maximal wavelength | Absorption width of 50% transmittance | Transmittance at 500 nm |
|---|---|---|---|
| Compound 1 | 584.0 nm | 66 nm | not less than 85% |
| Compound 13 | 598.0 nm | 66 nm | not less than 85% |
| Compound 29 | 590.5 nm | 74 nm | not less than 90% |
| Compound 41 | 590.0 nm | 69 nm | not less than 85% |
| Compound 43 | 582.0 nm | 68 nm | not less than 85% |
| Compound 44 | 578.5 nm | 68 nm | not less than 85% |
| Compound 46 | 604.5 nm | 77 mm | not less than 90% |

From the foregoing results, it can be seen that the filter for an electronic display device of the present invention selectively shields the light having such a wavelength that reduces the color purity and can provide a clear image.

According to the present invention, there can be provided filters for an electronic display device which selectively shield the light having such a wavelength that reduces the color purity, and thereby can provide clear images.

What is claimed is:

1. A filter for an electronic display device comprising a squarylium compound represented by formula (I):

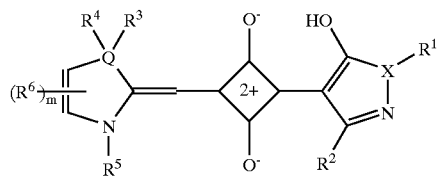

wherein X represents a nitrogen atom;
Q represents a carbon atom;
$R^1$ represents a hydrogen atom, an alkyl group optionally having substituent(s), an aryl group optionally having substituent(s), an aralkyl group optionally having substituent(s), or a heterocycle group optionally having substituent(s);
$R^2$ represents a hydrogen atom, a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s);
$R^3$ and $R^4$ independently represent a hydrogen atom, an alkyl group optionally having substituent(s), an aryl group optionally having substituent(s), an aralkyl group optionally having substituent(s), or a heterocycle group optionally having substituent(s), or $R^3$ and $R^4$ may be taken together with an adjacent carbon atom to form an alicyclic hydrocarbon ring optionally having substituent(s), or an heterocyclic ring optionally having substituent(s);
$R^5$ represents a hydrogen atom, an alkyl group optionally having substituent(s), an aryl group optionally having substituent(s), an aralkyl group optionally having substituent(s), or a heterocycle group optionally having substituent(s);
$R^6$ represents a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s); and
m represents an integer of 0–2, wherein when m is 2, then respective $R^6$s may be the same or different, or further two $R^6$s may be taken together with two carbon atoms to which each $R^6$ is adjacent to form an aromatic ring optionally having substituent(s).

2. A filter for an electronic display device comprising a squarylium compound represented by formula (Ib):

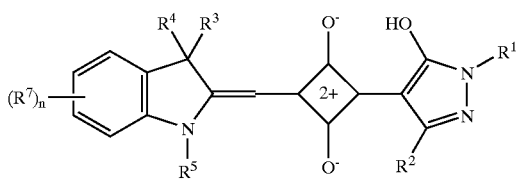

wherein $R^1$ represents a hydrogen atom, an alkyl group optionally having substituent(s), an aryl group optionally having substituent(s), an aralkyl group optionally having substituent(s), or a heterocycle group optionally having substituent(s);

$R^2$ represents a hydrogen atom, a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s);

$R^3$ and $R^4$ independently represent a hydrogen atom, an alkyl group optionally having substituent(s), an aryl group optionally having substituent(s), an aralkyl group optionally having substituent(s), or a heterocycle group optionally having substituent(s), or $R^3$ and $R^4$ may be taken together with an adjacent carbon atom to form an alicyclic hydrocarbon ring optionally having substituent(s), or an heterocyclic ring optionally having substituent(s);

$R^5$ represents a hydrogen atom, an alkyl group optionally having substituent(s), an aryl group optionally having substituent(s), an aralkyl group having substituent(s), or a heterocycle group optionally having substituent(s);

$R^7$ represents a halogen atom, an alkyl group optionally having substituent(s), an alkoxyl group optionally having substituent(s), an aralkyl group optionally having substituent(s), an aryl group optionally having substituent(s), a nitro group, a cyano group, a hydroxyl group, an amino group optionally having substituent(s), or a heterocycle group optionally having substituent(s); and n represents an integer of 0–4, wherein when n is 2–4, then respective $R^7$s may be the same or different, or further two $R^7$s may be taken together with two carbon atoms to which each $R^7$ is adjacent to form an aromatic ring optionally having substituent(s).

3. The filter for an electronic display device according to claims 1 or 2, which further comprises a binder.

* * * * *

UNITED STATES PATENT AND TRADEMARK OFFICE
CERTIFICATE OF CORRECTION

PATENT NO. : 6,818,262 B2
DATED : November 16, 2004
INVENTOR(S) : Ikuo Shimizu et al.

It is certified that error appears in the above-identified patent and that said Letters Patent is hereby corrected as shown below:

Column 1,
Line 21, "FILER" should read -- FITTER --.

Column 3,
Line 43, "ATOM;" should read -- ATOM, --.

Column 6,
Line 15, "etc.] A" should read -- etc.]. A --; and
Line 30, "etc.)" should read -- etc.). --.

Column 8,
Line 29, "is" should read -- in --.

Column 9,
Line 11, "etc.)" should read -- etc.). --.

Column 10,
Line 9, "(loge)" should read -- (log ε) --.

Column 12,
Line 33, "an" should read -- a --.

Column 13,
Line 9, "an" should read -- a --.

Column 14,
Line 3, "having" should read -- optionally having --.

Signed and Sealed this

Nineteenth Day of April, 2005

JON W. DUDAS
*Director of the United States Patent and Trademark Office*